United States Patent [19]

Villani et al.

[11] Patent Number: 4,939,092

[45] Date of Patent: Jul. 3, 1990

[54] PROTEINACEOUS DERIVATIVES CONTAINING IRON IN HIGHLY BIOAVAILABLE FORM, PREPARATION THEREOF AND PHARMACEUTICAL COMPOSITIONS CONTAINING THEM

[75] Inventors: Flavio Villani; Adriano Zamboni, both of Trecate, Italy

[73] Assignee: Unibois S.p.A., Novara, Italy

[21] Appl. No.: 263,542

[22] Filed: Oct. 27, 1988

[30] Foreign Application Priority Data

Nov. 13, 1987 [IT] Italy .................................. 22631 A/87

[51] Int. Cl.$^5$ ...................... C12N 9/36; A61K 33/26; C07K 15/00
[52] U.S. Cl. .................................... 435/206; 424/94.3; 424/94.61; 424/646; 424/647; 424/648; 530/400

[58] Field of Search ............ 435/206; 424/94.3, 94.61, 424/646, 647, 648; 530/400; 556/138

[56] References Cited

U.S. PATENT DOCUMENTS 4,493,829 1/1985 Sportoletti et al. ................. 530/400

FOREIGN PATENT DOCUMENTS 243322 10/1987 European Pat. Off. ............ 530/400

*Primary Examiner*—Robert A. Wax
*Attorney, Agent, or Firm*—Walter H. Schneider

[57] ABSTRACT

Iron proteinaceous derivatives, obtained from ferric or ferrous salts and lysozyme with glutaric or 1,2-cyclohexanedicarboxylic anhydride and their pharmaceutical use in the oral treatment of iron-deficiency anemia, are described.

5 Claims, No Drawings

PROTEINACEOUS DERIVATIVES CONTAINING IRON IN HIGHLY BIOAVAILABLE FORM, PREPARATION THEREOF AND PHARMACEUTICAL COMPOSITIONS CONTAINING THEM

This invention refers to proteinaceous derivatives able to bind high quantities of iron.

They are obtained through derivatization of lysozime by suitable anhydrides other than succinic anhydride and subsequent binding with iron. Thanks to precise and well controlled reaction conditions and to the use of suitable anhydrides, the obtained derivatives contain substantial quantities of highly bioavailable iron.

The discovery of iron in the human organism and its unreplaceable physiological role date back to early 1700 and are due to Giusmano, Galeazzi and Meneghini.

The determination of the iron contents in the human organism, rather arduous at first, was subsequently carried out by Widssowson E. M. et al., Clin. Sci., 1951, vol. 10, 113: the results indicated variable values in the tissues of approx. 3.5 g, of which 60–70% contained in the hemoglobin and in the myoglobin while a 20% remains stored in the liver, the spleen and the bone marrow as a labile combination from where it is taken in case of need.

The remaining 10–20% is firmly fixed in the tissues distributed in the various enzyme systems: catalase, cytochromes, peroxidase, ferroflavoproteins, transferrins, etc. (Boettcher E. W. et al., Nature, 1958, vol. 181, 490). The human organism satisfies its iron need partly by using the endogenous one and partly the one supplied by food.

The iron contained in food is firstly reduced to bivalent iron by the gastric juices and then absorbed at the duodenal level and by the first part of jejunum, thanks to the favourable pH of the first tract of the small intestine, and stored mostly in the liver.

The absorption through the intestinal mucous membrane seems to occur through an active transport mechanism influenced by the energetic availability of the mucous membrane cells. In case of illnesses due to iron-deficiency as in pregnancy, breast-feeding and infectious diseases, the most suitable therapy is the transfer of exogenous iron, which however is often coupled to undesired side-effects caused by the vehicle used.

The therapy has been based for a long time on oral administration of iron metal or of inorganic iron salts: ferrous iron is better absorbed than ferric one.

Absorption is increased by the succinic acid, by the iron chelating agents and by reducing substances such as ascorbic acid while it diminishes in association with a meal (Brise H. Acta Med. Scand., 1962, vol. 171, suppl. 376): moreover the absorption of iron varies in relation to the restoration of its contents in the organism (Solvel L. In: IRON METABOLISM London, Academic Press. 1970, p. 573), which makes its dosage difficult.

The side-effects of oral administration of ferrous or ferric iron are revealed at the gastro-intestinal level by deranges to the mucous membrane up to necrosis and perforation: allergic reactions such as tachycardia and sometimes anaphylactic shock and cardiocirculatory collapse are instead noticed after administration by intramuscolar route (ferrodextran) and by intravenous route (ferrodextrin).

To obviate to the above drawbacks, in 1957 were carried out preparations based on ferritin, the most important iron reserve protein, which immediately entered clinical practice due to its indubious advantages specially under the tolerability profile.

The Ferritin, extracted from bovine and equine spleen, is hydrosoluble, therefore easily administered by oral route, does not have gastrointestinal side-effects and constitutes in addition a reserve of iron which does not activate the intracellular proteins.

Nevertheless, as high cost and relative availability of extractive sources of ferritin limit its production and utilization, a new proteic vehicle of animal or vegetable origin for administration of iron has been sought.

Not all proteins which present a certain affinity for iron (serumproteins, ovalbumin, lactoprotein) can be used as a carrier as in the majority of cases insoluble complexes, where it is difficult to determine the amount of contained iron, are obtained.

It was thought recently that, because the succinyl derivatives of casein and of ovalbumin, more easily degradable from the protease and more emulsionable than the original protein (Gandhi S. K., Schultz J. R., Boughey F. W., Forsythe R. H. J. Food Sci., 1968, vol. 33, 163), are used as food additives (Evans M., Rons L., Petty J. H. Biochim. Biophys. Acta, 1971, vol. 243, 259), they can also be used as iron carrier (U.S. Pat. No. 4,493,829). Consequently, by succinylating the lactoprotein and then binding the succinylated protein with iron, a compound with a good iron contents, remarkable stability, able to precipitate at the stomach pH acid and to dissolve in the intestine basic medium, has been obtained.

EP-A No. 243322 discloses similar derivatives wherein succinylation has been replaced by acylation with other dicarboxylic acid anhydrides.

The proteins used both in EP-A No. 243322 and in U.S. Pat. No. 4,493,829 are not however precisely identifiable and they actually comprise a mixture of different proteins extracted from milk (casein is the major, but not unique, component), egg (ovalbumin is the major, but not unique, component), serum (albumin is the major, but not unique, component), soy, liver etc.

It has now been found that a protein derivative obtained by acylation of lysozyme with dicarboxylic acid anhydrides other than succinic anhydride, provides an ideal carrier for iron.

The iron complex according to the present invention shows, in comparison with the prior-art, a standardized and constant analytical profile which is a highly desirable feature for the industrial production of drugs. Lisozyme is in fact a well-defined enzyme which can be obtained in high purity, practically free from contaminants.

The iron complex of the present invention is also endowed with the following, other advantageous characteristics:
 ability of binding high amounts of iron;
 high bioavailability of iron;
 practically absence of toxicity or side-effects;
 stability of the complex.

The derivative of the invention is obtained by reaction, in aqueous solution, of lysozyme with dicarboxylic acid anhydrides chosen in the group consisting of glutaric anhydride, maleic anhydride and anhydride of cyclohexane dicarboxylic acid, under strictly controlled pH and temperature conditions.

The compound of the invention can be obtained by operating at pH comprised between 7.5 and 8, preferably about 30° C.; in conditions of high salinity, that is in buffered environment, at salts concentration comprised between 15% and 30% w/v, preferably around 20% w/v with excess of anhydride in respect to the lysozyme derivable groups.

It has been surprisingly found that operating for example with glutaric anhydride, derivatives at high degree of derivatization are obtained without difficulty; thus, at the conditions of Example 2 of U.S. Pat. No. 4,493,829, a product is obtained from lysozyme with glutaric anhydride, containing 11-14% by weight of glutaric residues, against 5% by weight of succinic residues.

Moreover, if the complexation with $Fe^{+++}$ occurs by means of salts such as glycerophosphate, citrate or by means of buffers such as to allow the maintaining of pH at values $\geq 6$, the $Fe^{+++}$ complexation turns out to be improved and the product obtained by subsequent acidification at pH3 shows a highly desirable analytic profile For the proposed therapeutic use, in the oral treatment of iron-deficient anemia, the derivatives subject of the invention are formulated in suitable pharmaceutical compositions by resorting to conventional recipients and techniques, like those described in Remington's Pharmaceutical Sciences Handbook, Hack Pub. Co., N.Y. U.S.A. Examples of such formulations comprise capsules, tablets, vials, granulates, powders and syrups containing from 10 to 50 mg of the invention's derivatives, per unit dose, administered from 2 to 4 times a day.

Non limiting examples of the invention are reported here below.

EXAMPLE 1

(a) 2 l of demineralized water are charged, at room temperature, into a 4 l reactor fitted with stirrer, thermometer and external thermostatic bath, in which 184 g of $KH_2PO_4$ 130 ml of NaOH 30% are then added and the mixture is stirred for 10 minutes.

The pH of the resulting buffer solution must be 8. Lysozyme (100 g) is then slowly added and the mixture is stirred at room temperature till complete dissolution.

At this point the external thermostatic bath is regulated at 30° C. and when the buffered proteic solution reaches this temperature, glutaric anhydride (160 g) is added in small portions.

The rhythm of these additions must be regulated in such a way to have a contained exothermic reaction so that internal temperature does not exceed 35° C. Once the adding process is over, the solution is kept under stirring for 3-4 hours to allow temperature to drop spontaneously to 25° C.

The slightly opalescent solution is filtered till clarity and the resulting solution is acidified with conc. HCl till complete precipitation of the product (pH 2.4-2.8).

This is filtered and washed with HCl 0.001 N, then dried and characterized by means of physico- chemical analyses (110 g).

(b) 100 g of lysozyme glutarate are dissolved in 2.4 l of distilled $H_2O$ by adding 33 ml of NaOH 4N (pH=7.5). A solution of 75 g of ferric glycerophosphate. $H_2O$ in 150 ml of $H_2O$ is slowly added. During the addition, the pH is kept $\geq$ 6 optionally adding NaOH 4N or suitable buffers. A brown solution at pH 7 is obtained which is stirred for 2 hours, then acidified with HCl 4N up to pH 3, obtaining the precipitation of the ferric complex.

Precipitation of the ferric derivative is thus obtained; the latter is then washed and filtered with HCL 0.01N to eliminate completely the un-bound iron.

The obtained solid is dissolved in water at pH 7 and clarified of the possible presence of modest amounts of insoluble matter.

The clear solution obtained is dialyzed and then lyophilized thus obtaining the final product (c) Characteristic of the acylated lysozyme glutarate obtained in (a)

Total glutaric acid: 15.8% (via gas-chromatography after hydrolysis of the sample with NaOH).

Free glutaric acid: 2% (via gas-chromatography).

Solubility at pH 8: Complete

Solubility at pH 3: nil

U.V. Spectrum: A solution at a 0.05 mg/ml concentration presenting a maximum absorption at 283 nm ($E^{1\%}_{1cm}=6$) and a maximum absorption at 220 nm ($E^{1\%}_{1cm}=39.2$)

I.R. Spectrum: Three enlarged bands of weak intensity at $1550\ cm^{-1}$, $1650\ cm^{-1}$ and $3300\ cm^{-1}$ Suspension in Nujol).

Electrophoresis: Unitary spot. Starch black detection. (Run on Cellulose acetate for 30 minutes using a 250 voltage)

HPLC: single peak at 36 minutes (Superose 6H/R column 30 cm×10 mm. PHARMACIA eluant buffer: Tris 0.05M/NaCl 0.15M $NaN_3$ 0.02% at pH 8.8, flow 0.5 ml/minute, detection 280 nm).

(d) Characteristic of the iron complex obtained in (b) (UB 1004)

$Fe^+$ titre: 33 3 mg/g (Value determined by spectrophotometry).

Total glutaric acid: 11.3% (via gas-chromatography after hydrolysis of the sample with NaOH).

Free glutaric acid: <0.1% (via gas-chromatography).

pH aqueous sol. 1%: 7.0

Solubility at pH 8: Complete

Precipitation with $(NH_4)_2SO_4$ at 30%: Complete

Solubility of the precipitate with $(NH_4)_2SO_4$ in water: Complete

U.V. Spectrum: A solution at a 0.05 mg/ml concentration presenting a maximum absorption at 290 nm and a flexion of absorption at 220 nm ($E^{1\%}_{1cm}=18.2$).

I.R. Spectrum: Three enlarged bands of weak intensity at $1530\ cm^{-1}$, $1650\ cm^{-1}$ and $3300\ cm^{-1}$ (Suspension in Nujol).

Electrophoresis: Unitary spot both at detection with ferrocyanide and with starch black (Run on Cellulose acetate for 30 minutes at 250 voltage).

HPLC: Main peak at 36 minutes (Superose 6H/R column 30 cm×10 mm. PHARMACIA eluant buffer: $K_2HPO_4$ 0.05M/NaCl 0.15M/$NaN_3$ 0.02% at pH 7.2, flow, 0.5 ml/min., detection 280 nm). Other peaks less than 10%.

EXAMPLE 2

Pharmaceutical forms

| Standard tablets (capsules) | |
|---|---|
| UB 1004 | mg 15 |
| Starch | mg 25 |
| binding and lubricating agents | mg 10 |
| Shock tablets (capsules) | |
| UB 1004 | mg 30 |
| Starch | mg 50 |

| -continued | |
|---|---|
| binding and lubricating agents | mg 20 |
| paediatric type effervescent sachets | |
| UB 1004 | mg 10 |
| effervescent mixture | mg 50 |
| sugar | mg 100 |
| various aromas | — |
| effervescent sachets for adults | |
| UB 1004 | mg 20 |
| effervescent mixture | mg 60 |
| sugar | mg 150 |
| natural aromas | — |
| syrup solution | |
| in 100 g of syrup vehicle | |
| UB 1004 | mg 200 |
| aromatized sugar syrup q.s. | g 100 |

COMPARATIVE EXAMPLE

Using casein and glutaric anhydride according to the procedures above described, a product having the following characteristics has been obtained.

(a) casein glutarate.

Total glutaric acid: 13% (via gas-chromatography after hydrolysis of the sample with NaOH).

Free glutaric acid: 0.1% (via gas-chromatography).

Solubility at pH 8: Complete

Solubility at pH 3: Unsoluble

U.V. Spectrum: A solution at 0.05 mg/ml concentration presents two maximum absorptions at 290 nm ($E^{1\%}_{1cm}=30$).

I.R.: Three enlarged bands of weak intensity at 1600 $cm^{-1}$, 1700 $cm^{-1}$ and 3500 $cm^{-1}$ (Suspension in Nujol).

Electrophoresis: Unitary spot. Starch black detection. (Run on Cellulose acetate for 30 minutes using a 250 voltage).

HPLC: single peak at 32 minutes and three secondary peaks at 16 minutes, 28.5 minutes and 45.5 minutes (Superose 6H/ R column 30 cm×10 mm. PHARMACIA eluant buffer: $K_2HPO_4$ 0.05M/NaCl 0.15M/$NaN_3$ 0.2% at pH 7.2, flow 0.5 ml/minutes, detection 280 nm).

(b) iron casein glutarate.

$Fe^+$ titre: 61.8 mg/gr (Value determined by spectrophotometry).

Total glutaric acid: 11.5% (Value determined by gas-chromatography after hydrolysis of the sample with NaOH)

Free glutaric acid: <0.1% (via gas-chromatography).

pH aqueous sol. 1%: 6.8

Solubility at pH 8: Complete

Precipitation with $(NH_4)_2SO_4$ at 30%: Complete

Solubility of the precipitate with $(NH_4)_2SO_4$ in water: Complete

U.V. Spectrum: A solution at 0.02 mg/ml concentration presents an absorption defined flow at 250 nm ($E^{1\%}_{1cm}=50$).

Electrophoresis: Unitary spot both at detection with ferrocyanide and with starch black (Run on Cellulose acetate for 30 minutes using 250 voltage).

HPLC: Main peak at 24 minutes. Two secondary peaks at 16.1 minutes and 37.7 minutes. (Superose 6H/R column 30 cm×10 mm. PHARMACIA eluant buffer: $K_2HPO_4$ 0.05M/NaCl 0.15M/$NaN_3$ 0.2 at pH 7.2, flow, 0.5 ml/min., detection 280 nm).

As it can be seen, the product deriving from casein glutarate shows in HPLC more than one peak because of lack of uniformity of the obtained product.

PHARMACOLOGICAL TESTS

The pharmacological tests have been carried out by comparing the product obtained according to Example 1 b with the products available on the market, that is: Ferritin, compound according to U.S. Pat. No. 4,493,829 (which, for brevity, will be referred to in the following tables as 282) and Ferrous Sulphate. In the aim of correctly evaluating activity, bio-availability and toxicity of the products under exam, they were suitably vehicled by means of dissolution in mixtures of $H_2O$/propylene glycol/sorbitol, in equal proportions, so as to obtain for the experimental tests solutions at identical $Fe^{+++}$ titre (4 mg/ml).

TABLE 1

| Antianemic activity. | | | | | | |
|---|---|---|---|---|---|---|
| | ERYTHROCYTES (.$10^6$/$mm^3$) | | | HEMOGLOBIN (g/100 ml) | | |
| GROUPS | 7 | 14 | 21 | 7 | 14 | 21 |
| CONTROL NORMAL | 6.64 ± 0.33 | 7.48 ± 0.27 | 7.39 ± 0.24 | 14.69 ± 0.69 | 15.73 ± 1.97 | 14.46 ± 1.41 |
| CONTROL DIET | 6.20 ± 0.58* | 6.36 ± 0.54** | 6.41 ± 0.47** | 12.59 ± 1.53** | 13.85 ± 1.25** | 13.55 ± 1.29 |
| DIET + UB 1004 | 7.20 ± 0.58** | 7.20 ± 0.48** | 7.13 ± 0.26** | 14.43 ± 1.13** | 15.70 ± 1.00** | 15.58 ± 0.97** |
| DIET + FERRITINE | 68.9 ± 0.39** | 6.99 ± 0.58** | 6.99 ± 0.13** | 13.88 ± 0.93** | 15.46 ± 0.93** | 14.43 ± 1.12 |
| DIET + 282 | 6.98 ± 0.35** | 6.72 ± 0.50 | 7.07 ± 0.29** | 15.06 ± 0.92** | 15.78 ± 1.42** | 14.59 ± 0.81* |
| DIET + FERROUS SULFATE | 7.07 ± 0.76** | 7.34 ± 0.46** | 6.94 ± 0.42* | 14.38 ± 1.91* | 15.63 ± 0.33** | 14.09 ± 1.50 |

| | | SYDEREMIA (μg/100 ml) | | |
|---|---|---|---|---|
| | GROUPS | 7 | 14 | 21 |
| | CONTROL NORMAL | 168.6 ± 42.9 | 140.1 ± 20.8 | 174.4 ± 25.6 |
| | CONTROL DIET | 112.0 ± 36.0** | 113.1 ± 27.6** | 143.1 ± 16.9** |
| | DIET + UB 1004 | 178.6 ± 57.1** | 177.5 ± 42.8** | 184.3 ± 31.8** |
| | DIET + FERRITINE | 196.3 ± 88.9** | 217.1 ± 52.7 | 227.6 ± 25.7** |
| | DIET + 282 | 163.6 ± 69.3* | 177.1 ± 23.4** | 166.0 ± 26.1* |
| | DIET + | 247.6 ± 87.0** | 198.4 ± 52.2** | 171.0 ± 19.9** |

TABLE 1-continued

Antianemic activity.

FERROUS
SULFATE

*p<0.05
**p<0.01

TABLE 2
ACUTE TOXICITY OF UB 1004 AFTER ORAL ADMINISTRATION IN THE MALE RAT

| DOSE (mg/Kg Fe = mg/Kg) | N° ANIMALS | N° DEAD ANIMALS | % DEATH-RATE |
|---|---|---|---|
| 1 — 25 = 367.5 | 10 | 0 | 0.00 |
| 2 — 50 = 735 | 10 | 0 | 0.00 |
| 3 — 100 = 1470 | 10 | 0 | 0.00 |
| 4 — 200 = 2940 | 10 | 0 | 0.00 |
| 5 — 400 = 5880 | 10 | 0 | 0.00 |

DL50 NOT DETERMINABLE

TABLE 3
GASTRIC TOLERABILITY: VALUES OF THE LESIONS FOUND ON THE GASTRIC MUCOSA OF RATS TREATED BY THE ORAL ROUTE T.I.D. AT DOSES EQUIVALENT TO 100 MG/KG OF IRON.

| N. Animal | 1 | 2 | 3 | 4 | 5 | 6 | 7 | Media |
|---|---|---|---|---|---|---|---|---|
| CONTROL | 0 | 0 | 0 | 0 | 0 | 0 | 0 | 0 |
| UB1004 | 0 | 0 | 0 | 0 | 0 | 0 | 0 | 0 |
| FERRITIN | 1 | 1 | 0 | 0 | 0 | 0 | 0 | 0.28 |
| 282 | 1 | 1 | 0 | 0 | 1 | 0 | 0 | 0.42 |
| FeSO4 | 1 | 2 | 1 | 1 | 3 | 1 | 3 | 1.70 |

CONCLUSIONS on the PHARMACOLOGICAL TESTS

The results reported and commented above allow to draw the following conclusions on the derivative of the invention, subject of the present study:

(1) the derivative presents a good bio-availability which manifests through a marked dose-related activity;

(2) it causes an increase of sideremia higher for intensity and duration than the one produced by ferritin and by 282, at equal iron concentration, as shown by the calculation of the pharmacokinetic parameters;

(3) it is very effective in restoring the normal hematologic (hemoglobin, G.R.) and hematochemical (sideremia) parameters altered by an iron-deficient diet administered to the rats to induce experimental anemia;

(4) it is non toxic at all and especially non gastrodamaging, not even at high dosages, which are at any rate unattainable in therapy, and is therefore to be preferred to the ferrous sulphate which is considerably toxic and harmful at the gastric level;

(5) finally, it constitutes an improvement over ferritin in that, while displaying similar and in some tests greater activity, is, as stressed in the introductory part, more easily available while maintaining the latter's therapeutic characteristics

We claim:

1. A ferric or ferrous complex of lysozyme acylated with glutaric anhydride or with the anhydride of 1,2-cyclohexanedicarboxylic acid.

2. A complex according to claim 1 wherein lysozyme is acylated with glutaric anhydride.

3. A complex according to claim 2 comprising 11–12% of glutaric residues.

4. A process for the preparation of the complex of claim 1 comprising the acylation of lysozyme with an excess of the anhydride at a pH between 7.5–8 and at a temperature from 25° to 35° C., subsequent dissolution of the acylated protein in diluted alkali and final precipitation from said solution by addition of a ferric or ferrous salt.

5. A pharmaceutical formulation for the treatment of iron deficient anemias containing as the active principle a complex according to claim 1 in admixture with a pharmaceutically acceptable carrier.

* * * * *

UNITED STATES PATENT AND TRADEMARK OFFICE
CERTIFICATE OF CORRECTION

PATENT NO.   : 4,939,092
DATED        : July 3, 1990
INVENTOR(S)  : Flavio Villani; Adriano Zamboni It is certified that error appears in the above-identified patent and that said Letters Patent is hereby corrected as shown below:

On the Title page, item [73] Assignee:, "Unibois S.p.A."

should read ---Unibios S.p.A.---.

Signed and Sealed this

Twenty-third Day of February, 1993

Attest:

STEPHEN G. KUNIN

*Attesting Officer*  *Acting Commissioner of Patents and Trademarks*